United States Patent [19]
Schafer et al.

[11] Patent Number: 6,091,795
[45] Date of Patent: Jul. 18, 2000

[54] AREA DETECTOR ARRAY FOR COMPUTER TOMOGRAPHY SCANNING SYSTEM

[75] Inventors: David A. Schafer, Natick; Simon George Harootian, Worcester; Sorin Marcovici, Lexington, all of Mass.

[73] Assignee: Analogic Corporation, Peabody, Mass.

[21] Appl. No.: 08/948,450

[22] Filed: Oct. 10, 1997

[51] Int. Cl.[7] .................................................. G01N 23/00
[52] U.S. Cl. ........................................ 378/19; 250/370.11
[58] Field of Search ............... 378/98.8, 19; 250/370.11, 250/370.09

[56] References Cited

U.S. PATENT DOCUMENTS

| | | | |
|---|---|---|---|
| 3,936,645 | 2/1976 | Iversen | 250/370.11 |
| 4,338,521 | 7/1982 | Shaw et al. | 250/366 |
| 4,914,301 | 4/1990 | Akai | 250/370.01 |
| 4,982,096 | 1/1991 | Fujii et al. | 250/367 |
| 5,059,800 | 10/1991 | Cueman et al. | 250/367 |
| 5,151,588 | 9/1992 | Kiri et al. | 250/208.1 |
| 5,319,693 | 6/1994 | Eberhard et al. | 378/19 |
| 5,355,309 | 10/1994 | Eberhard et al. | 364/413.15 |
| 5,473,658 | 12/1995 | Wallschlaeger | 378/19 |
| 5,510,622 | 4/1996 | Hu et al. | 250/367 |

FOREIGN PATENT DOCUMENTS 0 715 830  12/1996  European Pat. Off. .

*Primary Examiner*—Craig E. Church
*Attorney, Agent, or Firm*—McDermott Will & Emery

[57] ABSTRACT

A two-dimensional area detector array for a CT scanning system includes a set of alignment grids for aligning individual scintillator crystals with corresponding photodiodes and for preventing optical and electrical interference between adjacent photodiodes. The alignment grids thus facilitate efficient transfer of information from the scintillation crystals to the photodiodes and also permit the detector array to be constructed with many very small, very closely spaced individual detector elements. The alignment grids are preferably made of a substantially opaque material having a relatively low coefficient of thermal expansion. They provide a highly beneficial dimensional stability to the detector array under the typical operating conditions of the CT scanner.

23 Claims, 3 Drawing Sheets

AREA DETECTOR ARRAY FOR COMPUTER TOMOGRAPHY SCANNING SYSTEM

CROSS-REFERENCE TO RELATED APPLICATIONS

This application is related to pending U.S. application Ser. No. 08/671,716 (Attorney Docket No. ANA-93), filed on Jun. 27, 1996 in the name of Bernard M. Gordon and assigned to the assignee of the present invention.

This application is related to the following U.S. applications filed on even date herewith, of common assignee, the contents of which are incorporated herein in their entirety by reference:

"Computed Tomography Scanner Drive System and Bearing," invented by Andrew P. Tybinkowski et al. (Attorney Docket No. ANA-128);

"Air Calibration Scan for Computed Tomography Scanner with Obstructing Objects," invented by David A. Schafer et al. (Attorney Docket No. ANA-129);

"Computed Tomography Scanning Apparatus and Method With Temperature Compensation for Dark Current Offsets," invented by Christopher C. Ruth et al. (Attorney Docket No. ANA-131);

"Computed Tomography Scanning Target Detection Using Non-Parallel Slices," invented by Christopher C. Ruth et al. (Attorney Docket No. ANA-132);

"Computed Tomography Scanning Target Detection Using Target Surface Normals," invented by Christopher C. Ruth et al. (Attorney Docket No. ANA-133);

"Parallel Processing Architecture for Computed Tomography Scanning System Using Non-Parallel Slices," invented by Christopher C. Ruth et al. (Attorney Docket No. ANA-134);

"Computed Tomography Scanning Apparatus and Method Using Parallel Projections from Non-Parallel Slices," invented by Christopher C. Ruth et al. (Attorney Docket No. ANA-135);

"Computed Tomography Scanning Apparatus and Method Using Adaptive Reconstruction Window," invented by Bernard M. Gordon et al. (Attorney Docket No. ANA-136);

"Closed Loop Air Conditioning System for a Computed Tomography Scanner," invented by Eric Bailey et al. (Attorney Docket No. ANA-138);

"Measurement and Control System for Controlling System Functions as a Function of Rotational Parameters of a Rotating Device," invented by Geoffrey A. Legg et al. (Attorney Docket No. ANA-139);

"Rotary Energy Shield for Computed Tomography Scanner," invented by Andrew P. Tybinkowski et al. (Attorney Docket No. ANA-144).

TECHNICAL FIELD

The present invention relates to x-ray detector systems in CT scanners used to inspect baggage and packages for explosives, and more particularly to two-dimensional, or area, detector arrays used in such scanner systems.

BACKGROUND OF THE INVENTION

Modern baggage scanning systems in airports are increasingly employing computerized tomography (CT) scanning systems to scan and screen packages and luggage for explosive devices. X-ray—based scanning systems typically identify objects on the basis of relative density and radiopacity, whereas other systems can detect such devices on the basis of various other properties, such as atomic number. For example, it is known that explosives generally have a relatively high nitrogen content. Accordingly, a scanner which can distinguish materials on the basis of the atomic numbers of their constituents can be used to detect the presence of explosives.

Plastic explosives, because of their moldability, present a particular challenge to baggage scanning systems because they can be formed into geometric shapes that are difficult to detect. Most explosives capable of significantly damaging an aircraft weigh at least a pound and are sufficiently large in length, width, and height so as to be readily detectable by an X-ray scanner system regardless of the orientation of the explosive within the baggage. However, a plastic explosive powerful enough to damage an aircraft may be formed into a relatively thin sheet that is extremely small in one dimension and is relatively large in the other two dimensions. The detection of such forms of plastic explosives may be hindered because it may be difficult to see a thin sheet of the explosive material in the image, particularly when the sheet is disposed so that it is parallel to the direction of the X-ray beam as the sheet passes through the system.

Thus, detection of sheet explosives in baggage requires very attentive operators. The requirement for such attentiveness can result in greater operator fatigue, and fatigue as well as any distractions can result in a suspected bag passing through the system undetected.

Accordingly, a great deal of effort has been made to design a better baggage scanner. At least one of these designs, described in U.S. Pat. Nos. 5,182,764 and 5,367,552 to Peschmann et al. (hereinafter, the '764 Patent and '552 Patent, respectively), includes a CT scanner of the third-generation type. Such systems have been widely used in the medical imaging arts and typically include an X-ray source and an X-ray detector system secured, respectively, to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system includes a linear array of detectors disposed as a single row in a circular arc having a center of curvature at the focal spot of the X-ray source (i.e., the point within the X-ray source from which the X-rays emanate). The X-ray source generates a fan-shaped beam, or fan beam, of X-rays that emanates from the focal spot, passes through a planar imaging field, and is received by the detectors.

As is well known, a coordinate system is defined by X-, Y- and Z-axes, wherein the axes intersect and are all normal to one another at the "isocenter" (the center of rotation of the disk as the disk rotates about the rotation axis). The Z-axis is defined by the rotation axis and the X- and Y-axes are defined by, and lie within, the planar imaging field. The fan beam is thus defined as the volume of space defined between a point source (i.e., the focal spot) and the receiving surfaces of the detectors of the detector array exposed to the X-ray beam. Because the dimension of the receiving surfaces of the linear array of detectors is relatively small in the Z-axis direction, the fan beam is relatively thin in that direction.

Each detector generates an output signal representative of the intensity of the X-rays incident on that detector. Since the X-rays are partially attenuated as a function of the densities of objects in their path, the output signal generated by each detector is representative of the densities of all the objects disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection", and the angular orientation of the disk (and the corresponding angular orientations of the X-ray source and the detector array) during generation of a projection is referred to as the "projection angle". At each projection angle, the path of the X-rays from the focal spot to each detector, called a "ray", increases in cross-sectional dimension from a point source to the receiving surface area of the detector. The density measurement is considered to be magnified, because the receiving surface area of the detector area is larger than any cross-sectional area of the object through which the ray passes. As the disk rotates around the object being scanned, the scanner generates a plurality of projections at a corresponding plurality of projection angles. A CT image of the object may be generated from all the projection data collected at each of the projection angles using well-known algorithms.

To be of practical utility in any major airport, a baggage scanner should be capable of scanning a large number of bags at a very fast rate, e.g., on the order of three-hundred bags per hour or faster, and to provide this rate the scanner must scan an average sized bag at a rate of about 12 seconds per bag or less. CT scanners of the type described in the '764 and '552 Patents take a relatively long to generate the data for a single-slice CT image, because one revolution of the disk requires between about 0.6 and 2.0 seconds. Further, the thinner the slice of the beam through the bag for each image, the better the resolution of the image. Accordingly, the CT scanner should provide images of sufficient resolution to detect plastic explosives on the order of only a few millimeters thick. If 0.6 to 2.0 seconds are required for generation of data for each CT image, and the average bag can be assumed to be about 70 cm long, at the desired throughput rate of 300 bags per hour a conventional CT baggage scanner can only afford to generate an average of six or seven CT images per bag, since the bag must be moved and stopped at each location of a scan. Clearly, one cannot scan the entire bag within the time allotted for a reasonably fast throughput. Generating only six or seven CT images per baggage item leaves most of the item un-scanned.

One solution to this problem involves the use of a two-dimensional detector array. Such an array is typically made up of multiple rows and columns of individual detectors. Relatively rapid three-dimensional imaging can be accomplished using this radiation beam and detector array geometry.

Two-dimensional area detector arrays are disclosed in, for example, U.S. Pat. No. 5,059,800 to Cueman et al. and in pending U.S. application Ser. No. 08/671,716, filed on Jun. 27, 1996 in the name of Bernard M. Gordon, entitled "Quadrature Transverse CT Detection System", and assigned to the assignee of the present invention.

The detectors of the Cueman et al. array include many mosaic scintillation elements separated by a layer of reflective epoxy containing titanium dioxide to reduce optical crosstalk, or interference. One end of each scintillation element is adapted to receive x-rays, while the other end is adapted to transmit light to a photodiode coupled optically to it.

The detector array of the Gordon application, incorporated herein by reference, includes detectors which are longer in one direction than in another so as to provide enhanced image resolution in both the X-Y and Z planes.

Prior art two-dimensional detector arrays continue to suffer from lack of sufficient isolation of adjacent detector elements, which can result in optical and electrical crosstalk, or interference, between them. The small sizes of the individual detector elements and the spaces between them makes it difficult to isolate them sufficiently from one another to prevent such interference. In addition, insufficient alignment of the components and insufficient planarity of the detector arrays decrease the reliability of the detector systems and increase the costs of manufacturing, assembling, installing and replacing them.

Accordingly, it would be an advancement in the art to provide a two-dimensional detector array which minimizes or eliminates the problem of electrical and optical interference within an array of relatively small and closely-spaced detector elements.

SUMMARY OF THE INVENTION

The invention provides an area detector array for CT scanning systems which is highly efficient and sensitive, as well as cost-effective and reliable. Most importantly, as a result of its unique structure, the detector array of the present invention is highly dimensionally stable in the operating conditions of the scanning system, which can include vibration and fluctuations in temperature.

According to one aspect of the invention, an area detector array for a CT scanning system comprises:

a. A substrate for supporting the detector array;

b. A plurality of photodiodes arranged on the substrate in a two-dimensional array;

c. An element on the substrate for transmitting electrical signals generated by the photodiodes to a signal processing device; and d. A scintillator crystal assembly overlying and interfaced with the photodiode array.

The scintillator crystal assembly comprises a plurality of individual scintillator crystals, and means for arranging the crystals in a two-dimensional array corresponding to the photodiode array. The crystal assembly provides substantial dimensional stability to the detector array during operation of the scanning system. Each of the scintillator crystals is substantially aligned with and interfaced with a corresponding photodiode. In addition, each crystal and photodiode pair is substantially electrically and optically isolated from the other crystal and photodiode pairs.

In a preferred embodiment, a set of alignment grids is used to arrange and align the scintillator crystals with corresponding photodiodes. Each of the alignment grids has a plurality of cells adapted to receive and surround a photodiode or a scintillator crystal. Each of the alignment grids is also made of a substantially rigid, substantially opaque material having a relatively low coefficient of thermal expansion. In a preferred embodiment, at least one of the grids is substantially three-dimensional and is adapted for alignment of its cells with the photodiodes, and at least one of the grids is substantially planar and is adapted to align with the three-dimensional grid so that each of the scintillator crystals is substantially aligned with a corresponding photodiode.

In a preferred embodiment, the region between a scintillator crystal and a corresponding photodiode contains an optically transmissive medium, and the regions between and above adjacent scintillator crystals contain an optically reflective medium. The optically transmissive medium preferably has a refractive index in the range from approximately 1 up to the refractive index of the scintillator crystals.

According to another aspect of the invention, a method of making an area detector array for a CT scanning system comprises the steps of:

a. Providing a plurality of photodiodes and arranging them in a two-dimensional array on a substrate;

b. Establishing a signal transmitting path on the substrate and the photodiode array for transmitting electrical signals generated by the photodiodes to signal processing means; and c. providing a scintillator crystal assembly which includes a plurality of individual scintillator crystals, and means for arranging the scintillator crystals in a two-dimensional array corresponding to the photodiode array. Each of the scintillator crystals is substantially aligned with a corresponding photodiode so that each paired crystal and photodiode is substantially electrically and optically isolated from the other paired crystals and photodiodes. Substantial dimensional stability is thus provided to the detector array during operation of the scanning system.

The method can include the further steps of placing an optically transmissive medium within the region between each scintillator crystal and its corresponding photodiode, and placing an optically reflective material above and within the regions between adjacent scintillator crystals.

According to still another aspect of the invention, a CT scanning system, which includes a radiation source, means for detecting radiation emitted from the source and providing signals representative of the detected radiation, means for moving the source and detecting means about and relative to an object to be scanned, means for supplying power to the radiation source, and means for processing the signals to acquire image data relating to the object being scanned, further includes an area detector array as previously described.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be had to the following detailed description taken in connection with the accompanying drawings, in which.

Like elements in the FIGURES are indicated with like reference numerals.

DETAILED DESCRIPTION OF THE DRAWINGS

Figure 1:
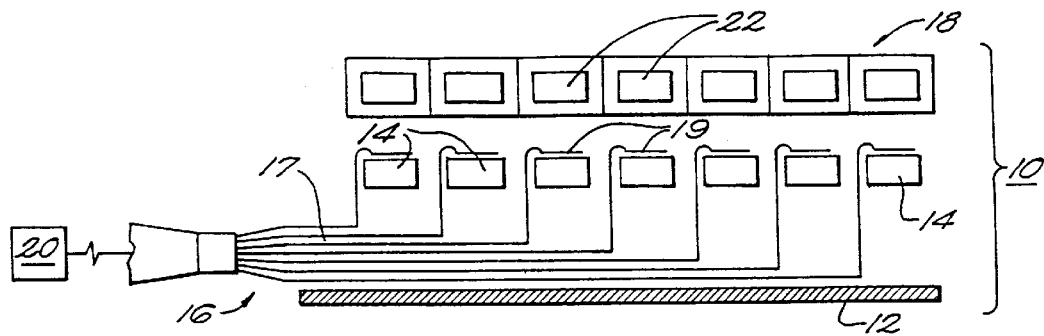
FIG. 1 is a simplified side view of an area detector array according to the invention.

The area detector array of the present invention includes a large number of relatively small individual detector elements, or scintillation crystals, arranged in a two-dimensional pattern or array which provides a three-dimensional scan of an object. The detector array incorporates a multifunctional structure comprising a set of alignment grids which function both to align the scintillation crystals with the photodiodes and also to isolate the individual photodiode/crystal pairs from one another to prevent optical cross-talk and electrical interference. The alignment grids also provide substantial dimensional stability to the array during operation of the scanning system.

The detector array 10 of the present invention is illustrated schematically in FIGS. 1–4. A substrate 12 supports the detector array. Photodiodes 14 are arranged on the substrate in a two-dimensional array. In a preferred embodiment, a single array comprises 72 photodiodes arranged in six rows of twelve photodiodes each. The substrate also supports means 16 for transmitting electrical signals generated by the photodiodes. The signal transmitting means 16 delivers electrical signals to signal processing means 20 for image reconstruction.

The signal transmission means 16 can include, for example, electrically conductive circuit paths printed into the substrate, or an electrically conductive interconnect layer 17 disposed on the substrate, and associated electrically conductive leads 19 from each photodiode to the electrical pathway to establish an electrical connection between each photodiode and the signal processing means 20.

A scintillator crystal assembly 18 is disposed over the photodiode array and includes a number of scintillator crystals 22 and means for arranging the crystals in a two-dimensional array which corresponds to the photodiode array. Each of the scintillator crystals 22 is substantially aligned with and interfaced with a corresponding photodiode 14 and yet is also substantially optically and electrically isolated from surrounding crystals. The detector array is also substantially dimensionally stable under the typical operating conditions of the CT scanning system, which may include, for example, vibration and/or temperature fluctuations.

Figure 2:
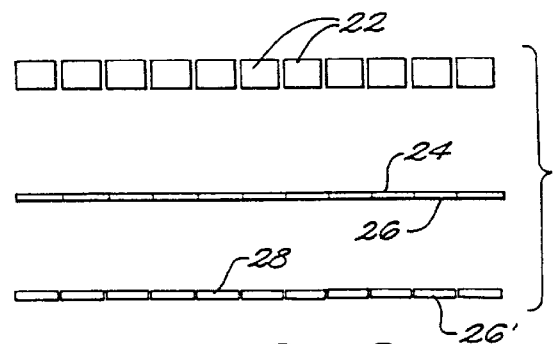
FIG. 2 is a simplified side view of a scintillator crystal assembly according to the invention.
Figure 3:
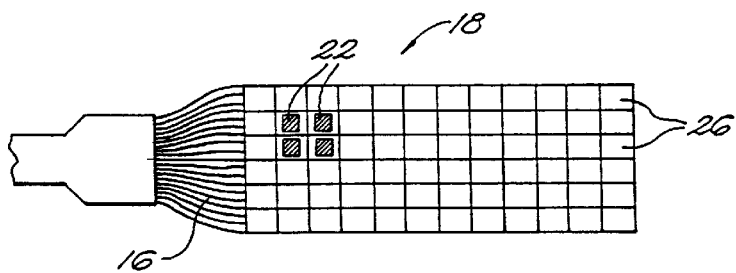
FIG 3 is a simplified plan view of a portion of the area detector array.

The scintillator crystals 22 of the assembly 18 are arranged in a two-dimensional array corresponding to the photodiode array by means of a set of alignment grids which are incorporated directly into the detector array 10. As shown in FIG. 2, at least one of the alignment grids 24 is substantially planar and includes a number of cells or openings 26. Each of the cells 26 is of a sufficient dimension to receive and substantially align with a scintillator crystal 22, as shown in FIG. 3. The cells 26 of the planar grid are relatively dimensionally stable. Another alignment grid 28 is substantially three-dimensional, i.e., it has a height dimension in addition to a length and width, and is also substantially rigid. It also includes a number of cells 26' corresponding to the cells of the first alignment grid 24. Each of the cells of the three-dimensional alignment grid 28 is substantially aligned with a corresponding cell of the planar alignment grid 24 and thus with a scintillator crystal 22.

In a preferred embodiment, at least one three-dimensional grid and at least one planar grid are employed in the assembly. The three-dimensional alignment grid 28 is preferably made of an optically opaque material which has a relatively low coefficient of thermal expansion, so as to lend structural support and stability to the detector array during operation of the scanner. Suitable materials for the three-dimensional alignment grid include, for example, glass, fiberglass, plastic and opaque ceramic.

The planar alignment grid is preferably made of a material which is relatively dimensionally stable under thermal and mechanical stresses. Suitable materials for the planar alignment grid include, for example, stainless steel, opaque ceramic, and glass-based materials. Optical opacity and dimensional stability are critical features of the alignment grids.

The alignment grids 24 and 28 provide a structural framework for the scintillator crystals 22 in the detector array which ensures the correct alignment of the crystals with corresponding photodiodes 14 and provides dimensional stability to the crystal assembly. As shown in FIG. 3, the cells 26, 26' of the respective alignment grids 24, 28 are each sized to accommodate and align a single scintillator crystal. The three-dimensional alignment grid 28 sits atop the photodiode array and electrical interconnections 17 on the substrate and establishes individual wells or cells directly over the photodiode array for each scintillator crystal.

Because the wire leads 19 from the photodiodes may be relatively fragile, they should preferably be protected from damage. The three-dimensional alignment grid 28 additionally serves as a standoff between the photodiode array and the scintillator crystal assembly so that the crystals 22 cannot rest directly on corresponding underlying photodiodes 14 and wire leads 19. In a preferred embodiment, the height of the grid 28 is at least as great as the height of the photodiode 14 and its associated electrical interconnect layer 17, and wire lead 19.

Figure 4:
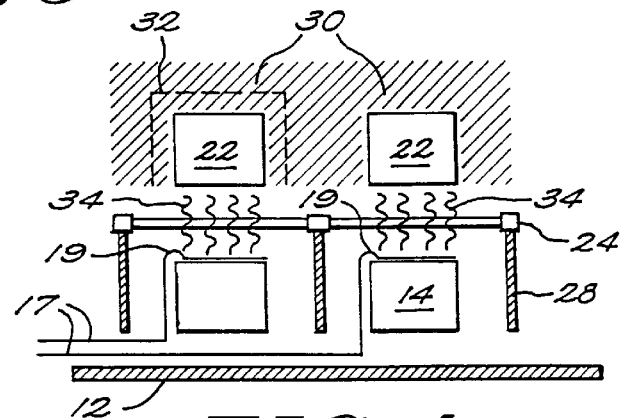
FIG. 4 is a detail view of a portion of the area detector array of FIG. 1.

As shown in FIG. 4, the scintillator crystals 22 are surrounded on up to all sides, other than the side closest to a corresponding photodiode 14, by an optically reflective material 30, such as, for example, an epoxy filled with titanium dioxide. In a preferred embodiment, the optically reflective material 30 can include a layer, coating or foil 32 of aluminum or other reflective material. This layer 32 is also preferably located around up to all sides of the scintillator crystal, other than the side facing a corresponding photodiode.

The region between a scintillator crystal 22 and a corresponding photodiode 14 contains an optically transmissive medium 34 to facilitate transmission of light from the crystal to the photodiode. The optically transmissive medium 34 preferably has a refractive index ranging from approximately 1 up to the refractive index of the scintillator crystals, which is typically about 2.5. Some suitable optically transmissive materials include, for example, air, glass, silicone, or polymeric materials such as an epoxy.

The substrate 12 can be made of any structural material which is suitable for supporting the photodiode and scintillator crystal array, as well as the electrical interconnect layer and signal transmission means. Suitable materials for the substrate include, for example, plastic, glass, fiberglass and ceramics. The substrate 12 is preferably substantially planar, although substrates which occupy a three-dimensional volume are considered to be within the scope of the invention.

Figure 5:
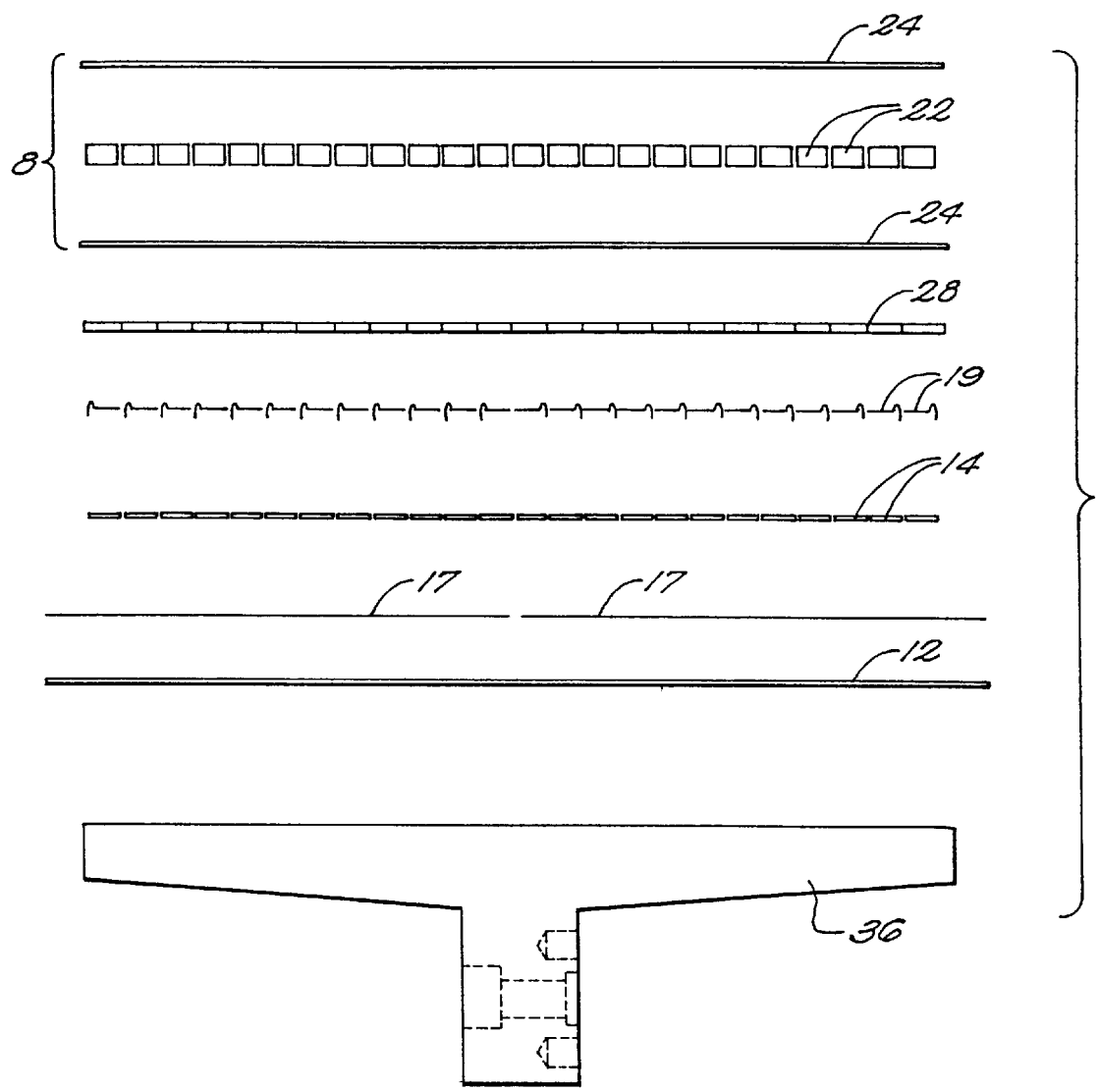
FIG. 5 is a simplified side view of a pair of area detector arrays mounted on a mounting block.

FIG. 5 is an exploded view of a detector assembly according to the invention. The detector array is mounted on a mounting block 36 which can be made of, for example, a metal such as steel. In a preferred embodiment, two detector arrays having a total of 144 scintillation crystals and 144 corresponding diodes are mounted and aligned head to head on the mounting block. The mounting block 36 is then secured to the rotatable disk with screws, bolts or the like.

An electrical interconnect layer 17 associated with the signal transmission means 16 comprises a network of electrical leads printed onto the substrate 12. The leads 17 provide electrical connections between each photodiode and the signal transmission means 16.

Disposed on top of the substrate 12 and leads 17 are the photodiodes 14, arranged in a two-dimensional array. A typical array includes six rows of twelve photodiodes in each row. Disposed on each photodiode 14 is a wire lead 19 which electrically connects the photodiode 14 to the underlying interconnect network 17.

A substantially three-dimensional, opaque and relatively rigid alignment grid 28 is then placed over the photodiode array so that each photodiode 14 is located within a cell 26' of the grid and optically isolated from adjacent photodiodes.

The scintillator crystal assembly 18 includes at least one, and preferably two, substantially planar alignment grids 24. Each grid 24 defines an array of cells 26 into which the scintillator crystals 22 are placed so as to align with the underlying photodiodes 14. The advantage of two planar alignment grids 24 is that enhanced dimensional and structural stability is obtained, especially during thermal and mechanical stresses on the array, such as during heat treatment and cure of epoxies used in the array. Warpage and distortion of the array when subjected to mechanical or thermal stresses are substantially avoided when at least one alignment grid 24 is used with the scintillator crystals.

As mentioned previously, the region between a scintillator crystal and a corresponding photodiode is preferably filled with an optically transmissive medium, such as air, silicone, transparent polymers, or glass. The regions between and above adjacent scintillator crystals are filled with an optically reflective medium, such as titanium-containing epoxy or a reflective paint or foil.

Figure 6:
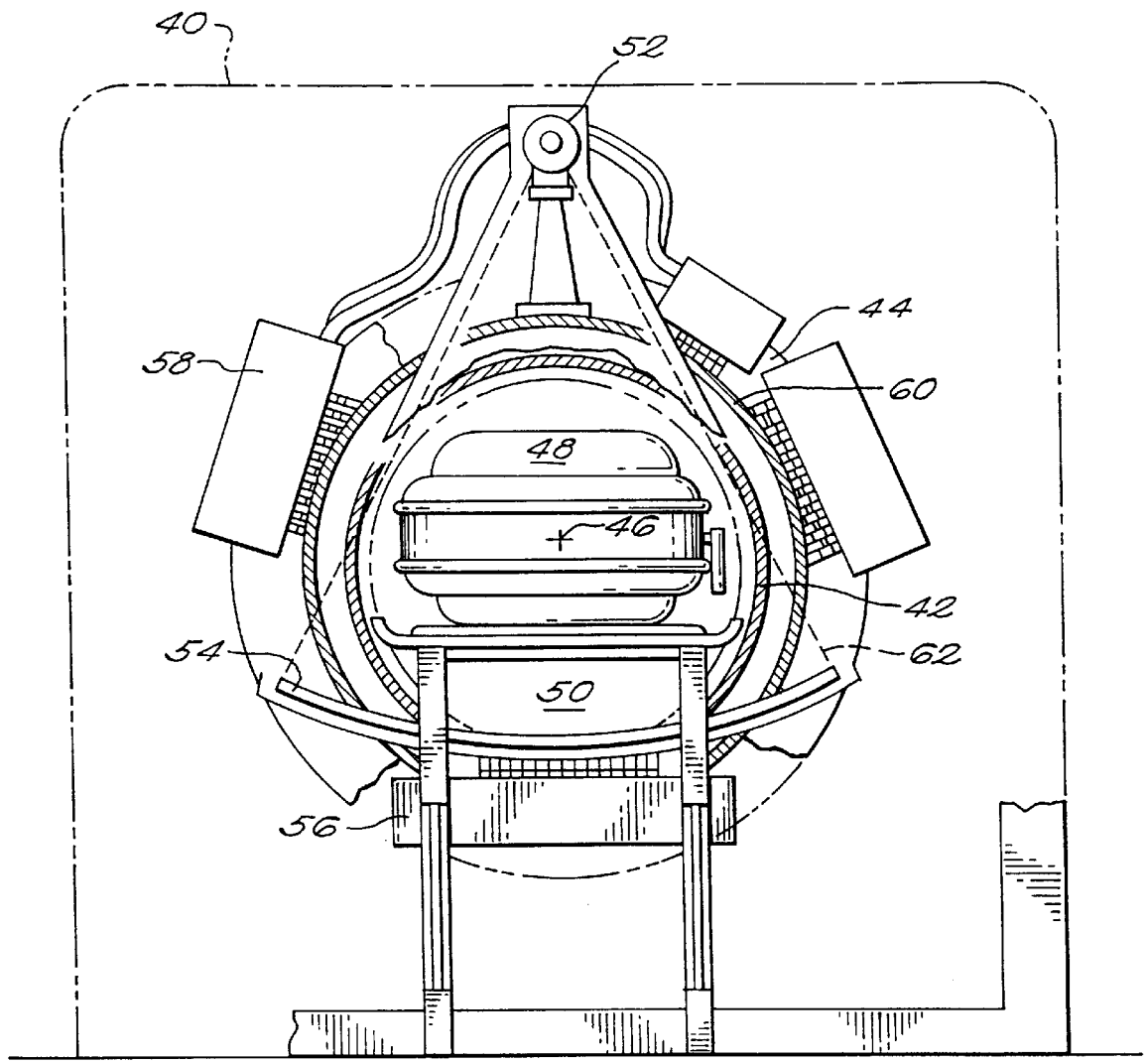
FIG. 6 is an axial view of a CT scanning system employing area detector arrays according to the present invention.

A CT scanning system employing area detector arrays according to the invention is shown in FIG. 6. The CT scanning system 40 includes an annular shaped rotating platform, or disk, 42 disposed within a gantry support 44 for rotation about a rotation axis 46 that is preferably parallel to the direction of travel of the baggage 48. Rotating platform 42 defines a central aperture 50 through which a conveyor system (not shown) transports the baggage 48. System 40 includes an X-ray tube 52 and a two-dimensional detector array system 54 which are disposed on diametrically opposite sides of the platform 42. System 40 further includes a data acquisition system 56 for receiving and processing signals generated by detector array 54, and an X-ray tube control system 58 for supplying power to, and otherwise controlling the operation of, X-ray tube 52. The system 40 is also preferably provided with a computerized system (not shown) for processing the output of the data acquisition system 56 and for generating the necessary signals for operating and controlling the system 40. The computerized system can also include a monitor (not shown) for displaying information including generated images. System 40 also includes shields 60, which may be fabricated from lead, for example, for preventing radiation from propagating beyond the gantry.

In operation, X-ray tube 52 generates a pyramid- or cone-shaped beam 62 of X-rays that pass through a three-dimensional imaging field, through which baggage 48 is transported by the conveying system. After passing through the baggage disposed in the imaging field, cone beam 62 is received by detector array 54 which in turn generates signals representative of the densities of exposed portions of baggage 48. The beam 62 therefore defines a scanning volume of space. Platform 42 rotates about its rotation axis 46, thereby rotating X-ray source 52 and detector array 54 about baggage 48 as the baggage is continuously transported through central aperture 50 by the conveyor system so as to generate a plurality of projections at a corresponding plurality of projection angles. In a well-known manner, signals from the detector array 54 can be initially acquired by data acquisition system 56, and subsequently processed by a computerized system (not shown) using CT scanning signal processing techniques. The processed data can be displayed on a monitor and/or can also be further analyzed by the computerized system to determine the presence of a material having the density and/or molecular weight of sheet explosives. If such data is present, suitable means can be provided for indicating the detection of such material to the operator or monitor of the system, for example, by providing an indication on the screen of a monitor, by sounding an audible or visual alarm, and/or by providing an automatic ejection device for removing the suspect bag from the conveyor for further inspection, or by stopping the conveyor so that the suspect bag can be inspected and/or removed.

A method of making an area detector array according the invention includes the steps of providing a substrate for the array, providing plurality of photodiodes, and arranging the photodiodes in a two-dimensional array on the substrate. A preferred arrangement of photodiodes is in six rows of twelve photodiodes each, for a total of 72 photodiodes arranged on a single substrate.

A signal transmitting path is established on the substrate and the photodiode array for transmitting electrical signals generated by the photodiodes to signal processing means.

A scintillator crystal assembly is then provided, the assembly comprising a plurality of individual scintillator crystals, and a set of alignment grids for arranging the crystals in a two-dimensional array corresponding to the photodiode array. Each of the scintillator crystals is substantially aligned with a corresponding photodiode within the grids so that each crystal and photodiode pair is substantially electrically and optically isolated from the other crystal and photodiode pairs.

The method can include the further steps of placing an optically transmissive medium within the region between each scintillator crystal and its corresponding photodiode, and placing an optically reflective material above and within the regions between adjacent scintillator crystals.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An area detector array for a CT scanning system, said detector array comprising:
   a. A substrate for supporting the detector array;
   b. A plurality of photodiodes arranged on the substrate in a two-dimensional array;
   c. means on said substrate for transmitting electrical signals generated by the photodiodes to signal processing means; and
   d. A scintillator crystal assembly overlying and interfaced with said photodiode array, said crystal assembly comprising:
      i. a plurality of individual scintillator crystals, and
      ii. a set of alignment grids for arranging said scintillator crystals in a two-dimensional array corresponding to the photodiode array, wherein said alignment grids provide substantial dimensional stability to the detector array during operation of the scanning system,
   wherein each of said scintillator crystals is substantially aligned with and interfaced with a corresponding photodiode, and each crystal and photodiode pair is substantially electrically and optically isolated from the other crystal and photodiode pairs.

2. An area detector array according to claim 1, wherein each of said alignment grids has a plurality of cells adapted for alignment of at least one of a photodiode and a scintillator crystal therein, each of said grids being substantially rigid and made of a material which is substantially opaque and which has a relatively low coefficient of thermal expansion, wherein at least one of said grids is substantially three-dimensional and is adapted for alignment of said cells with said photodiodes, and wherein at least one of said grids is substantially planar and is adapted to align with said three-dimensional grid so that each of said scintillator crystals is substantially aligned with a corresponding photodiode.

3. An area detector array according to claim 2, wherein the region between a scintillator crystal and a corresponding photodiode contains an optically transmissive medium, and wherein the regions between and above adjacent scintillator crystals contain an optically reflective material.

4. An area detector array according to claim 3, wherein said optically transmissive medium has a refractive index in the range from approximately 1 up to the refractive index of said scintillator crystals.

5. An area detector array according claim 4, wherein said optically transmissive medium is selected from the group consisting of glass, silicone and polymers.

6. An area detector array according to claim 4, wherein said optically transmissive medium is air.

7. An area detector array according to claim 3, wherein said optically reflective material includes titanium dioxide.

8. An area detector array according to claim 7, wherein said optically reflective material includes a metallic foil, layer or coating.

9. An area detector array according to claim 3, wherein said planar alignment grid is made of a material selected from the group consisting of metal, ceramic and glass.

10. An area detector array according to claim 2, wherein the height of each of the cells of said three-dimensional alignment grid is not less than the height of each of said photodiodes and said signal transmission means.

11. An area detector array according to claim 10, wherein said three-dimensional alignment grid is made of glass.

12. An area detector array according to claim 2, wherein said set of alignment grids comprises one substantially three-dimensional grid and two substantially planar grids.

13. An area detector array according to claim 1, wherein said substrate is substantially planar.

14. An area detector array according to claim 13, wherein said substrate is made of a material selected from the group consisting of ceramic, glass, fiberglass and plastic.

15. An area detector array according to claim 14, further comprising a mounting block adapted to support at least one of said substrates.

16. An area detector array according to claim 15, wherein said mounting block is adapted to support two of said substrates.

17. An area detector array according to claim 1, wherein said signal transmission means comprises an electrically conductive interconnect layer disposed on said substrate and establishing an electrical connection from each photodiode to said signal processing means.

18. A method of making an area detector array for a CT scanning system, said method comprising the steps of:
   a. Providing a plurality of photodiodes and arranging said photodiodes in a two-dimensional array on a substrate;
   b. Establishing a signal transmitting path on said substrate and said photodiode array for transmitting electrical signals generated by said photodiodes to signal processing means; and
   c. providing a scintillator crystal assembly comprising:
      i. a plurality of individual scintillator crystals, and
      ii. a set of alignment grids for arranging said scintillator crystals in a two-dimensional array corresponding to the photodiode array, wherein said alignment grids provide substantial dimensional stability to the detector array during operation of the scanning system,
   and substantially aligning each of said scintillator crystals with a corresponding photodiode so that each crystal and photodiode pair is substantially electrically and optically isolated from the other crystal and photodiode pairs.

19. A method according to claim 18, comprising the further steps of:
   d. Placing an optically transmissive medium within the region between each scintillator crystal and its corresponding photodiode; and
   e. Placing an optically rejective material above and within the regions between adjacent scintillator crystals.

20. In a CT scanning system including a radiation source, means for detecting radiation emitted from said source and providing signals representative of the detected radiation, means for moving said source and detecting means about and relative to an object to be scanned, means for supplying power to said radiation source, and means for processing said signals to acquire image data relating to said object being scanned, an area detector array comprises:
   a. A substrate for supporting the detector array;
   b. A plurality of photodiodes arranged on the substrate in a two-dimensional array;
   c. means on said substrate for transmitting electrical signals generated by the photodiodes to signal processing means; and
   d. A scintillator crystal assembly overlying and interfaced with said photodiode array, said crystal assembly comprising:
      i. a plurality of individual scintillator crystals, and
      ii. a set of alignment grids for arranging said scintillator crystals in a two-dimensional array corresponding to the photodiode array, wherein said alignment grids provide substantial dimensional stability to the detector array during operation of the scanning system,
   wherein each of said scintillator crystals is substantially aligned with and interfaced with a corresponding photodiode, and each crystal and photodiode pair is substantially electrically and optically isolated from the other crystal and photodiode pairs.

21. A CT scanning system according to claim 20, wherein each of said alignment grids has a plurality of cells adapted for alignment of at least one of a photodiode and a scintillator crystal therein, each of said grids being substantially rigid and made of a material which is substantially opaque and which has relatively low coefficient of thermal expansion, wherein at least one of said grids is substantially three-dimensional and is adapted for alignment of said cells with said photodiodes, and wherein at least one of said grids is substantially planar and is adapted to align with said three-dimensional grid so that each of said scintillator crystals is substantially aligned with a corresponding photodiode.

22. A CT scanning system according to claim 21, wherein the region between a scintillator crystal and a corresponding photodiode contains an optically transmissive medium, and wherein the regions between and above adjacent scintillator crystals contain an optically reflective material.

23. A CT scanning system according to claim 21, wherein said set of alignment of grids comprises one substantially three-dimensional grid and two substantially planar grids.

* * * * *